(12) United States Patent
Weber et al.

(10) Patent No.: US 6,758,990 B2
(45) Date of Patent: Jul. 6, 2004

(54) STABILIZING AGENT FOR HYDROXYLAMINE SOLUTIONS

(75) Inventors: Markus Weber, Ludwigshafen (DE); Hans-Josef Sterzel, Dannstadt-Schauernheim (DE); Eckhard Ströfer, Mannheim (DE); Otto Watzenberger, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/204,344

(22) PCT Filed: Feb. 14, 2001

(86) PCT No.: PCT/EP01/01605
§ 371 (c)(1),
(2), (4) Date: Aug. 20, 2002

(87) PCT Pub. No.: WO01/62710
PCT Pub. Date: Aug. 30, 2001

(65) Prior Publication Data
US 2003/0026751 A1 Feb. 6, 2003

(30) Foreign Application Priority Data
Feb. 22, 2000 (DE) .......................... 100 08 080

(51) Int. Cl.[7] ............................................. C09K 15/24
(52) U.S. Cl. ........................................ 252/403; 423/265
(58) Field of Search ........................... 252/403; 423/265

(56) References Cited

U.S. PATENT DOCUMENTS

| | | | |
|---|---|---|---|
| 3,145,082 A | 8/1964 | Rausch et al. ................. | 23/190 |
| 3,480,391 A | 11/1969 | Carlos et al. .................. | 23/190 |
| 3,544,270 A | 12/1970 | Carlos et al. .................. | 23/190 |
| 4,102,858 A | 7/1978 | Minagawa et al. ............. | 260/45 |
| 4,110,306 A | 8/1978 | Minagawa et al. ............. | 260/45 |
| 4,245,125 A | 1/1981 | Wirth et al. ................... | 568/680 |
| 4,482,626 A * | 11/1984 | Twist et al. ................... | 430/380 |
| 4,551,318 A | 11/1985 | Grosskinsky et al. ......... | 423/265 |
| 4,576,804 A | 3/1986 | Grosskinsky et al. ......... | 423/265 |
| 4,629,613 A | 12/1986 | Grosskinsky et al. ......... | 423/265 |
| 4,634,584 A | 1/1987 | Grosskinsky et al. ......... | 423/265 |
| 4,778,669 A | 10/1988 | Fuchs et al. ................... | 423/387 |
| 5,703,323 A * | 12/1997 | Rothgery et al. .............. | 149/88 |
| 5,783,161 A | 7/1998 | Schneider et al. ............. | 423/265 |
| 5,906,805 A * | 5/1999 | Chang et al. .................. | 423/265 |
| 6,179,937 B1 * | 1/2001 | Leveritt et al. ................ | 149/45 |

FOREIGN PATENT DOCUMENTS

| | | |
|---|---|---|
| CA | 2048899 | 2/1992 |
| DE | 40 25 788 | 2/1992 |
| EP | 0 147 742 | 7/1985 |
| EP | 0 516 933 | 12/1992 |
| JP | 4878099 | 1/1972 |
| JP | 51-132242 | 11/1976 |
| JP | 58069841 | 4/1983 |
| JP | 58069842 | 4/1983 |
| JP | 58069843 | 4/1983 |
| JP | 58069844 | 4/1983 |

OTHER PUBLICATIONS

Rodgers, et al., Inorg.Chem, 1987, 26, 1622–1625, "Ferric Ion Sequestering Agents . . . ".*

Hajela et al. "A Tris–hydroxymethyl–Substituted Derivative of Gd–TREN–Me–3,2–HOPO: An MRI Relaxation Agent with Improved Efficiency"J. Am. Chem. Soc. vol. 122 (2000) pp. 11228–11229.

Lockhoff "An Access to Glycoconjugate Libraries through Multicomponent Reactions" Angew. Chem. Int. Ed. vol. 37 No. 24 (1998) pp. 3436–3439.

Vögtle et al. "4–(Diemethylamino)—8–hydroxychinolin als neuer Chelatligand und als donorverstärkte Endgurppe on Podanden" Chem. Ber. vol. 118 (1985) pp. 1556–1563.

Vögtle et al. "Synthese und Selektivtät neuartiger vierarmiger nichtcyclischer Neutralliganden" Chem. Ber. vol. 112 (1979) pp. 899–907.

Vögtle et al. "Noncyclic Crypates" Angew. Chem. Int Ed. Engl. vol. 16 No. 8 (1977) pp. 548–549.

* cited by examiner

*Primary Examiner*—Matthew A. Thexton
(74) *Attorney, Agent, or Firm*—Keil & Weinkauf

(57) ABSTRACT

Hydroxylamine solutions stabilized using tri(4-(2,3-dihydroxyphenyl)-4-oxabutyl)amine, tri(4-(2,3-dihydroxyphenyl)-4-keto-3-azabutyl)amine or salts thereof, and methods of stabilizing hydroxylamine solutions using these compounds.

3 Claims, No Drawings

STABILIZING AGENT FOR HYDROXYLAMINE SOLUTIONS

The present invention relates to stabilized hydroxylamine solutions comprising at least one compound of the formula (I) or (II) as stabilizer, to the use of compounds of the formula (I) or (II) as stabilizer in hydroxylamine solutions, and to methods of stabilizing hydroxylamine solutions.

The present invention further relates to tri(4-(2,3-dihydroxyphenyl)-4-keto-3-azabutyl)amine of the formula

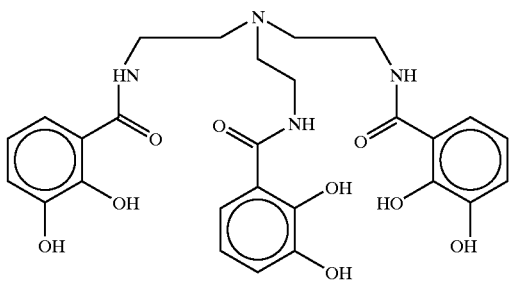

Basic or neutral solutions comprising hydroxylamine in the form of the free base enjoy numerous applications, for example, in the synthesis of fine chemicals or in the electronics industry.

It is known that such solutions are unstable and undergo decomposition to ammonia, nitrogen, nitrogen oxides, and water, so that transport and storage of such solutions is problematic.

In order to retard the decomposition, a stabilizer is added to the solutions. Stabilizers already proposed include the following:

thioglycolic acid (JP-A-58069843), glycerol monoethers and ethylene oxide adducts thereof (DE-A-2919554), hydroxyanthraquinones (DE-A-3343600), hydroxyquinolines (DE-A-3345734), polyhydroxyhexano-1,4-lactone (DE-A-3345733), anthocyanins (DE-A-3347260), hydroxyquinaldines, flavones, benzonitrile, N-phenyl-N-hydroxythiourea (DE-A-3601803), flavans (DE-A-3343599), thiosulfates, mercaptobenzothiazoles, mercaptoalkanols, mercaptothiazolines, thiuram disulfides, thioureas (EP-A-516933), the tetrasodium salt of ethylenediaminetetraacetic acid, the trisodium salt of N-hydroxyethylethylenediaminotriacetic acid, polyvinylpyrrolidone or poly-N-vinyl-5-ethyl-2-oxazolidinone (U.S. Pat. No. 3,145,082), amide oximes (U.S. Pat. No. 3,480,391), hydroxamic acids (U.S. Pat. No. 3,480,391), hydroxyureas (U.S. Pat. No. 3,544,270), dipyridyl compounds (JP-A-58069842), aminoquinolines (JP-A-58069844), phenanthrolines (JP-A-58069841), and polyhydroxyphenols (JP-A-4878099).

A disadvantage of these stabilizers is that they do not stabilize a hydroxylamine solution sufficiently for prolonged storage.

As a stabilizer which permits longer storage of a hydroxylamine solution, DE-A-19 547 759 proposed trans-1,2-diaminocyclohexane-N,N,N',N'-tetraacetic acid.

Although this stabilizer permits a longer storage period than those mentioned above, there is a further need for a prolongation of the possible storage period of hydroxylamine solutions.

It is an object of the present invention to provide a stabilizer for hydroxylamine solutions which permits a better possibility of stabilization, especially long-term stabilization, of hydroxylamine solutions.

We have found that this object is achieved by the stabilized hydroxylamine solutions defined at the outset, comprising at least one compound of the formula (I) or (II) as stabilizer, the use of compounds of the formula (I) or (II) as stabilizers in hydroxylamine solutions, methods of stabilizing hydroxylamine solutions and compounds of the formula (II).

The compounds of the formula (I) or (II) may be used as they are in the form of salts with organic acids, such as formic acid, acetic acid, benzoic acid, or, preferably, inorganic acids, such as sulfuric acid, nitric acid, phosphoric acid, phosphorous acid, preferably a hydrohalic acid, especially hydrogen chloride or hydrogen bromide.

Suitable compounds in accordance with the invention are tri(4-(2,3-dihydroxyphenyl)-4-oxabutyl)amine of the formula

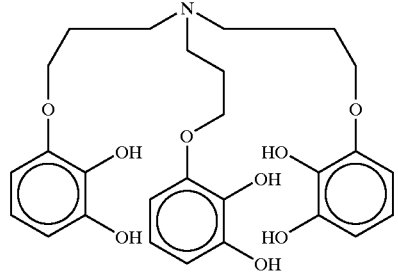

and tri(4-(1,2-dihydroxyphenyl)-4-keto-3-azabutyl)amine of the formula

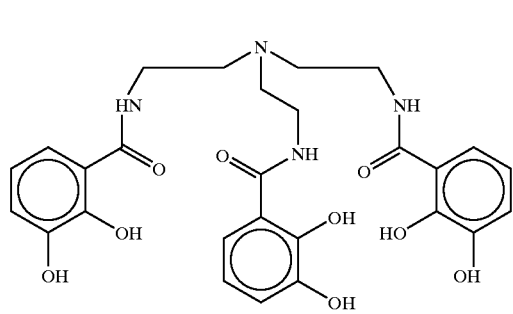

and also the salts thereof, preferably with hydrogen halide, especially hydrogen chloride or hydrogen bromide, such as
tri(4-(1,2-dihydroxyphenyl)-4-keto-3-azabutyl)amine hydrochloride,
tri(4-(1,2-dihydroxyphenyl)-4-keto-3-azabutyl)amine hydrobromide,
tri(4-(1,2-dihydroxyphenyl)-4-oxabutyl)amine hydrochloride, and
tri(4-(1,2-dihydroxyphenyl)-4-oxabutyl)amine hydrobromide.

The stabilized hydroxylamine solutions of the invention comprise at least one, such as 1, 2, 3 or 4, preferably 1 or 2, especially 1, compound of the formula (I) or (II) in free form or in the form of one or more at least partly neutralized salts; i.e., free compound of the formula (I) or (II) is present in the mixture with one or more salts of one or more compounds of the formula (I) or (II) in the mixture as the stabilizer. Similarly, the stabilized hydroxylamine solutions of the invention may comprise at least one, such as 1, 2, 3 or 4, preferably 1 or 2, especially 1, compound of the formula (I) or (II) in the form of one or more fully neutralized salts.

The stabilized hydroxylamine solutions of the invention comprise hydroxylamine in the form of the free base or an at least partly neutralized hydroxylamine salt; i.e., free hydroxylamine is present in a mixture with the hydroxylamine salt.

The stabilizers employed in accordance with the invention may be used to stabilize all kinds of hydroxylamine solutions. They may be aqueous solutions or solutions of hydroxylamine in an organic solvent, such as methanol, ethanol, n-propanol, isopropanol, acetone, tetrahydrofuran, etc., or mixtures of water and organic solvents. The stabilizers employed in accordance with the invention are likewise soluble in the solvents in which hydroxylamine is soluble.

Hydroxylamine solutions are generally obtained by reacting a hydroxylammonium salt, especially hydroxylammonium sulfate, hydroxylammonium chloride and hydroxylammonium phosphate, with an appropriate base, such as ammonia, sodium hydroxide, potassium hydroxide or calcium hydroxide. In the case of full neutralization of the hydroxylammonium salt a solution is obtained which contains free hydroxylamine and the salt originating from the base cation and the acid anion present in the hydroxylammonium salt. Some or all of the salt may be separated off. The hydroxylammonium salt may also be neutralized only partly with the base. In that case a solution is obtained which contains not only free hydroxylamine and the above-mentioned salt but also unreacted hydroxylammonium salt. All these solutions may be stabilized in accordance with the invention, the nature of the anion in the hydroxylammonium salt being uncritical.

The stabilized hydroxylamine solutions of the invention comprise the compounds of the formula (I) or (II) in an amount sufficient for stabilization. They preferably contain from 0.001 to 20% by weight (from 10 to 200,000 ppm), in particular 0.001 to 10% by weight, with particular preference from 0.01 to 5% by weight, with very particular preference from 0.02 to 2% by weight, of compound of the formula (I) or (II), based on the hydroxylamine content. The hydroxylamine concentration is generally from 1 to 100% by weight, in particular from 1 to 70% by weight, based on the overall weight of the solution.

The stabilizer may be added before or after neutralization of the hydroxylamine salt, but preferably before neutralization.

The compounds of the formula (I) or (II) are effective within a wide temperature range. Thus they stabilize hydroxylamine solutions in the range from −20° C. to 130° C., preferably from −10° C. to 100° C. However, they are also suitable as stabilizers even at markedly higher temperatures under the pressures required to liquefy the solution.

The examples below illustrate the invention without restricting it. The hydroxylamine concentrations reported in the examples are determined by redox titration.

EXAMPLES

A 50 ml round-bottomed glass flask was charged with 20 ml of 50% strength hydroxylamine solution, and 300 ppm (m/m) of stabilizer as per Table 1, based on the mass of hydroxylamine, were added.

The flask was held at room temperature, or heated to 100° C. using an oil bath and held at this temperature. The hydroxylamine contents of the stabilized solutions at 100° C. were determined after 15 hours by redox titration of samples. To do this, samples of defined quantity were withdrawn from the solutions, boiled for 5 minutes with an excess of ammonium iron(III) salt solution in sulfuric acid, and the iron(II) salt formed was back-titrated with cerium (IV) salt solution. The endpoint was determined potentiometrically.

The flask was held at 100° C. until rapid decomposition of the hydroxylamine ensued. At this point in time, the stabilizer has broken down to such an extent that it does not afford sufficient protection against decomposition of the hydroxylamine.

From Table 1 it is evident that the compounds of the formula (I) or (II) are able to stabilize hydroxylamine solutions the longest.

TABLE 1

| Addition | Hydroxylamine content of the solution [%] after 15 h | Time to decomposition [h] |
| --- | --- | --- |
| None | 25 | — |
| Thioacetamide | 49.5 | 40 |
| Thiourea | 49.5 | 40 |
| Thiouracil | 48.9 | 20 |
| Trithiocyanuric acid | 49.4 | 22 |
| Trans-1,2-diaminocyclohexane-N,N,N',N'-tetraacetic acid | 49.7 | 75 |
| Comp. of formula (I) as chloride | 49.7 | >100 |
| Comp. of formula (II) as bromide | 49.8 | >100 |

We claim:

1. A stabilized hydroxylamine solution comprising as stabilizer at least one compound selected from the group consisting of tri(4-(2,3-dihydroxyphenyl)-4-oxabutyl) amine, tri(4-(2,3-dihydroxyphenyl)-4-keto-3-azabutyl) amine, and salts thereof.

2. A stabilized hydroxylamine solution containing from 0.001 to 20% by weight, in particular from 0.001 to 10% by weight, preferably from 0.01 to 5% by weight, with particular preference from 0.02 to 2% by weight, based on hydroxylamine, of at least one compound selected from the group consisting of tri(4-(2,3-dihydroxyphenyl)-4-oxabutyl) amine, tri(4-(2,3-dihydroxyphenyl)-4-keto-3-azabutyl) amine, and salts thereof.

3. A method of stabilizing a hydroxylamine solution, which comprises bringing a compound selected from the group consisting of tri(4-(2,3-dihydroxyphenyl)-4-oxabutyl) amine, tri(4-(2,3-dihydroxyphenyl)-4-keto-3-azabutyl) amine, and salts thereof together with a hydroxylamine solution.

* * * * *